United States Patent [19]
Kauphusman et al.

[11] Patent Number: 5,792,070
[45] Date of Patent: Aug. 11, 1998

[54] RECTAL THERMOSENSING UNIT

[75] Inventors: James V. Kauphusman, Champlin; Jonathan L. Flachman, Minneapolis; Bruce H. Nielson, Brooklyn Park, all of Minn.

[73] Assignee: Urologix, Inc., Minneapolis, Minn.

[21] Appl. No.: 708,089

[22] Filed: Aug. 30, 1996

[51] Int. Cl.$^6$ ............................................................ A61B 5/00
[52] U.S. Cl. .................................................................. 600/549
[58] Field of Search ............................. 128/736, 692; 606/31, 33, 42; 607/96–102, 138; 600/549

[56] References Cited

U.S. PATENT DOCUMENTS

| | | | |
|---|---|---|---|
| 4,046,139 | 9/1977 | Horn | 128/2 H |
| 4,311,154 | 1/1982 | Sterzer et al. | 128/804 |
| 4,662,383 | 5/1987 | Sogawa et al. | 128/784 |
| 4,676,258 | 6/1987 | Inokuchi et al. | 128/804 |
| 4,813,429 | 3/1989 | Eshel et al. | 128/736 |
| 4,924,863 | 5/1990 | Sterzer | 606/27 |
| 4,950,267 | 8/1990 | Ishihara et al. | 606/12 |
| 4,967,765 | 11/1990 | Turner et al. | 128/785 |
| 5,106,360 | 4/1992 | Ishiwara et al. | 600/2 |
| 5,234,004 | 8/1993 | Hasceot et al. | 607/116 |
| 5,277,201 | 1/1994 | Stern | 607/98 |
| 5,304,214 | 4/1994 | Deford et al. | 607/105 |
| 5,335,669 | 8/1994 | Tihom et al. | 128/736 |
| 5,391,197 | 2/1995 | Burdette et al. | 607/97 |
| 5,404,881 | 4/1995 | Cathaud et al. | 128/653.1 |
| 5,474,071 | 12/1995 | Chapelon et al. | 128/660.03 |
| 5,484,400 | 1/1996 | Edwards et al. | 604/22 |
| 5,487,740 | 1/1996 | Sulek et al. | 606/15 |
| 5,496,271 | 3/1996 | Burton et al. | 604/54 |

FOREIGN PATENT DOCUMENTS

| | | |
|---|---|---|
| 0 105 677 | 9/1983 | European Pat. Off. . |
| 0 248 758 | 5/1987 | European Pat. Off. . |
| 0 253 677 | 7/1987 | European Pat. Off. . |
| 0 370 890 | 11/1989 | European Pat. Off. . |
| 0 459 535 | 11/1989 | European Pat. Off. . |
| 0 519 958 | 3/1991 | European Pat. Off. . |
| 0 485 323 | 11/1991 | European Pat. Off. . |
| 0 646 359 | 10/1994 | European Pat. Off. . |
| 0 646 360 | 10/1994 | European Pat. Off. . |
| 63-177867 | 7/1988 | Japan . |
| WO 91/13650 | 3/1991 | WIPO . |
| WO 93/02748 | 7/1992 | WIPO . |
| WO 94/26178 | 5/1994 | WIPO . |

OTHER PUBLICATIONS

"Transurethral Microwave Thermothrapy for Benign Prostatic Hypertrophy" by Blute, *Mediguide to Urology*, vol. 4, Issue 6, pp. 1–8, 1991.

"Microwave Applicators for Localized Hyperthermia Treatment of Malignant Tumors" by Mendecki et al., *Journal of Bioengineering*, vol. 1, pp. 511–518, 1977.

"Thermometry Considerations in Localized Hyperthermia", by Cetas et al., *Med. Phys*, 5(2), Mar./Apr. 1978, pp. 79–91.

"Radiofrequency–Induced Hyperthermia in the Prostate", by J. Scheiblich et al., *Journal of Microwave Power*, 1982, pp. 472–478.

"Microwave Applicator for Transurethral Hyperthermia of Benign Prostatic Hyperplasia", by Astrahan et al., *Int. J. Hyperthermia*, 1989, vol. 5, No. 3, 283–296.

"Single–Session Transurethral Microwave Thermotherapy for the Treatment of Benign Prostatic Obstruction", by Carter et al., *Journal of Endourology*, vol. 5, No. 5, 1991, pp. 137–144.

"Interstitial Temperature Measurements During Transurethral Microwave Hyperthermia" by Astrahan et al., *The Journal of Urology*, vol. 1445, pp. 304–308, Feb. 1991.

*Primary Examiner*—Francis Jaworski
*Attorney, Agent, or Firm*—Kinney & Lange

[57] ABSTRACT

A rectal thermosensing unit for sensing temperature of a patient's rectal tissue includes a temperature sensing device and an inflatable balloon defining a void interior. The balloon is coupled to and supports the temperature sensing device. Inflation of the balloon positions and maintains the temperature sensing device in contact with the rectal tissue without compressing the rectal tissue.

12 Claims, 7 Drawing Sheets

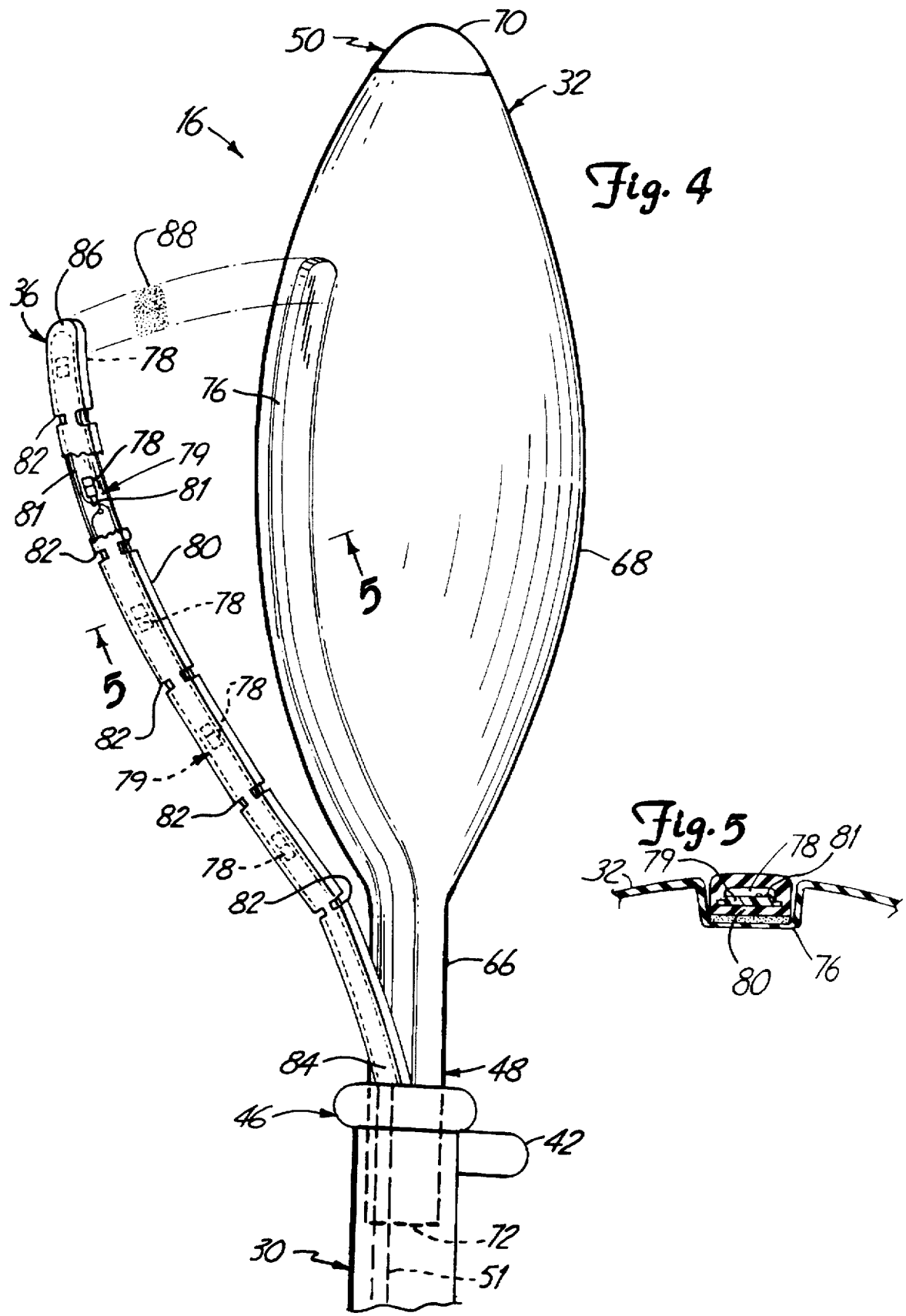

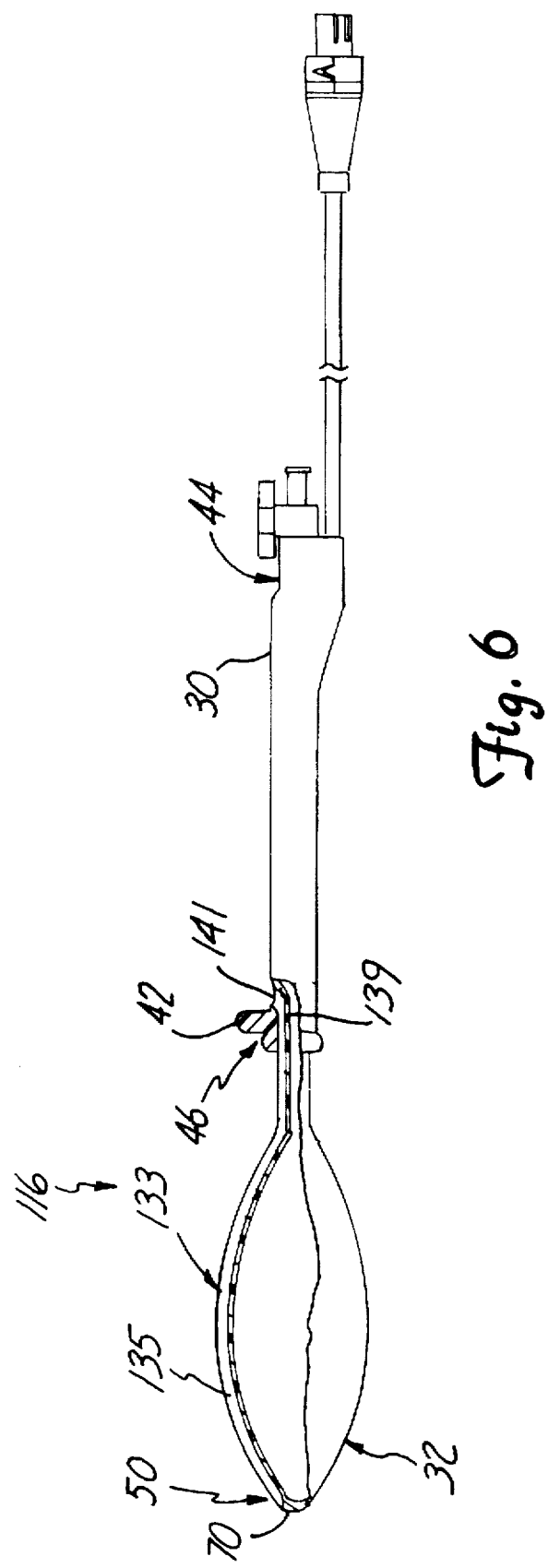

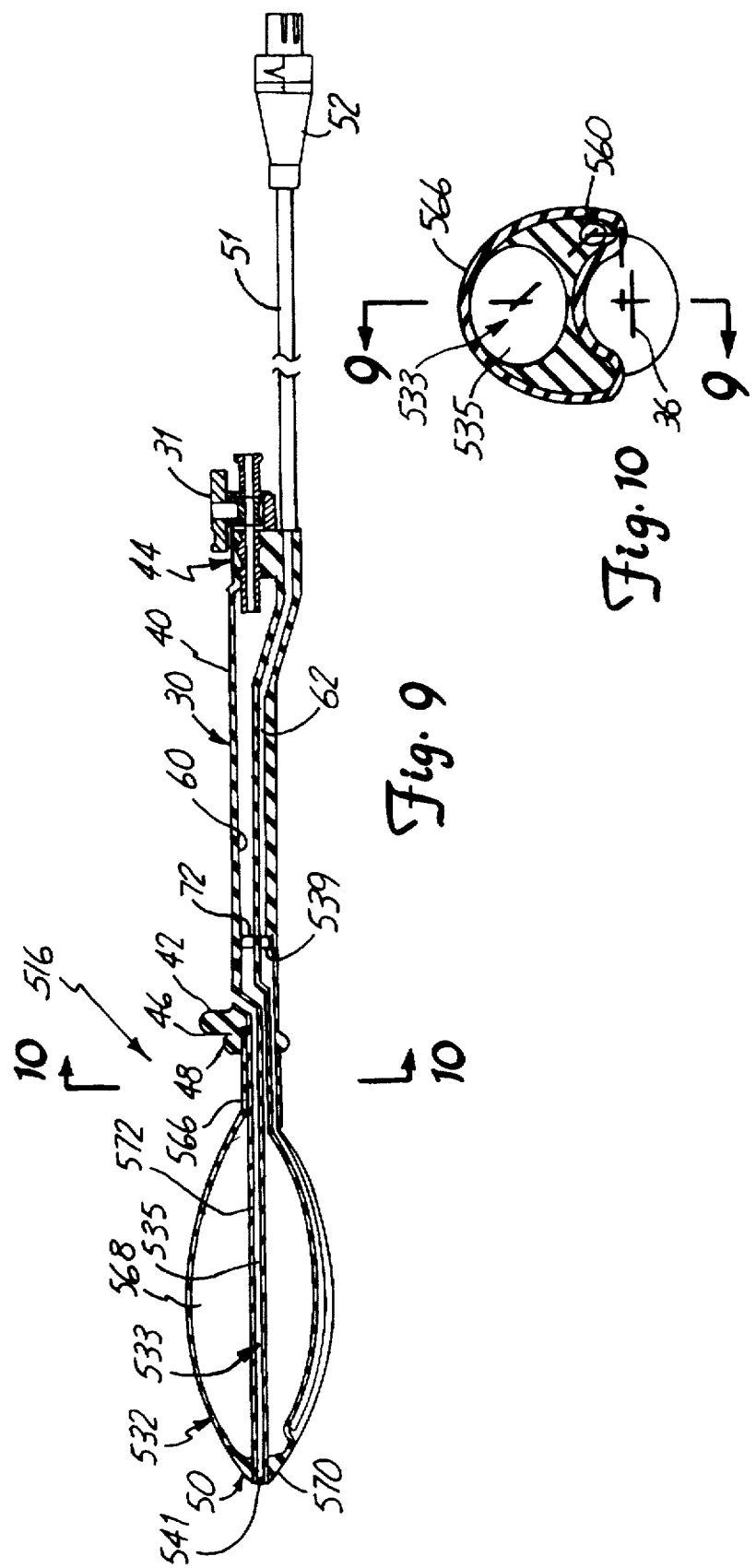

RECTAL THERMOSENSING UNIT

BACKGROUND OF THE INVENTION

The present invention relates to thermosensing units or probes for sensing rectal temperature of a patient. In particular, the present invention relates to a method and apparatus for sensing temperature of rectal tissue wherein a balloon supporting the temperature sensing device is inflated so as to position and maintain the temperature sensing device in contact with the rectal tissue.

Transurethral thermal therapy (T3) offers a non-surgical treatment of benign prostatic hyperplasia (BPH). During transurethral thermal therapy, it is advantageous to measure and monitor the temperature of tissue adjacent to the prostate to control the inducement or application of heat to prevent unnecessary damage to otherwise healthy tissue surrounding the diseased tissue. Typically, temperature of tissue surrounding the prostate is measured and monitored with a probe having temperature sensing elements that are inserted through the anus into the rectum of the patient. The probe supports the temperature sensing elements within the rectum as the sensing elements sense the temperature of rectal tissue adjacent the prostate to provide the physician with essential information for controlling the location and degree of heat induced or applied to the area of the prostate.

To effectively sense the temperature of tissue surrounding the prostate, several types of probes or temperature sensing devices have been proposed. For example, Cathaud et al. U.S. Pat. No. 5,404,881 discloses a transrectal probe having a body made of a flexible self-supporting polymer material having a degree of flexibility enabling the body to comply with the shape of the rectum. The probe body includes sensor means for sensing temperature within the rectum. Despite the transrectal probe's flexibility, improper insertion of the probe may traumatize the rectal tissue of the patient's rectum, providing discomfort to the patient and prolonging the treatment recovery. In addition, because the transrectal probe has substantially the same diameter along its axial length, the transrectal probe is susceptible to becoming dislodged or removed from the interior of the rectum, resulting in incorrect temperature measurements.

Alternatively, probes having substantially rigid bodies and including a lateral balloon for locking the probe body in a selected position within the rectum have been proposed. An example of such a probe is disclosed in document EP/A/0 248 758 in which the microwave applicator is locked in position in the rectum by a lateral balloon. The balloon displaces the applicator laterally within the body opening and presses the side of the applicator firmly against the rectal tissue within the rectum. Although the lateral balloon secures the applicator within the rectum, the applicator has a tendency to deform the wall of the rectum and compress it. Compression or displacement of the wall of the rectum creates several problems. First, compression of the rectal wall significantly reduces blood flow. Because blood flow is essential for removing heat from the wall of the rectum and tissue adjacent the prostate to protect otherwise healthy tissue from thermal damage, compression of the wall by the lateral balloon may cause significant overheating and damage to the otherwise healthy tissue. Second, displacement of the rectal wall interferes with accurate treatment of the prostate region. It has been found that precise control of the volume of tissue to which heat is applied is essential for treatment of BPH while minimizing damage to otherwise healthy tissue. Unintended and unaccounted for displacement of the rectal wall interferes with the controlled application of heat to the prostate region. Furthermore, as with the flexible transrectal probe, improper insertion of the substantially rigid applicator sleeve into the rectum may traumatize rectal tissue, causing discomfort to the patient and prolonging the treatment recovery period.

A third type of proposed temperature sensing probe is disclosed in Hascoet et al. U.S. Patent No. 5,234,004. The probe disclosed in Hascoet et al. comprises a generally rigid probe body having an inflatable element inflated with an ionic solution to form a balloon which extends around a second end of the probe body. The probe includes temperature sensors which are provided on the probe body itself or inside the balloon to detect temperature of the rectal tissue facing the prostate. Because the temperature sensors are secured to an inside of the balloon, manufacture of the probe of Hascoet et al. is more complex and costly.

Moreover, insertion of the sensing probe of Hascoet et al. is also likely to traumatize rectal tissue. Although the probe of Hascoet et al. includes a balloon which surrounds the second end of the probe body and has a larger surface area than the laterally extending balloon in document EP/A/0 248 758, the shape of the probe balloon of Hascoet et al. is generally spherical. As a result of its shape, the balloon also compresses rectal tissue to reduce blood flow and make the rectal tissue susceptible to thermal damage during hyperthermia treatment. In addition, the probe body itself of Hascoet et al. also adds weight to the sensing probe and may cause the probe to withdraw from within the rectum.

Each of the proposed rectal thermosensing devices either severely compress rectal tissue to risk thermal damage to the rectal tissue during hyperthermia treatment or are susceptible to becoming repositioned or dislodged from the rectum during treatment. As a result, there is a continuing need for a rectal thermosensing device that maintains its position within the rectum without compressing the rectal tissue and without causing discomfort to the patient.

SUMMARY OF THE INVENTION

The present invention is an improved rectal thermosensing unit for sensing temperature of rectal tissue forming a patient's rectum. The unit includes a temperature sensing device and an inflatable balloon defining a void interior. The balloon is coupled to and supports the temperature sensing device. Inflation of the balloon causes the balloon to assume its shape as closely as possible so as to engage the rectal wall without compressing the adjacent tissue. This in turn positions and maintains the temperature sensing device in contact with the rectal tissue.

In one preferred embodiment of the present invention, the temperature sensing device includes a plurality of spaced temperature sensors supported by an elongate flexible strip which is coupled to an exterior surface of a wall of the balloon. The balloon wall forms a groove which receives the elongate flexible strip supporting the spaced temperature sensors. Preferably, the flexible temperature sensing strip is formed with the handle as part of a unitary structure.

BRIEF DESCRIPTION OF THE DRAWINGS

FIG. 4 is an enlarged perspective view of a balloon and a temperature sensing device of the rectal thermosensing unit.

FIG. 5 is an enlarged fragmentary cross-sectional view of the rectal thermosensing unit taken along lines 5—5 of FIG. 4.

FIG. 6 is a side elevational view of a rectal thermosensing unit according to a first alternate embodiment of the present invention with portions shown in section.

FIG. 9 is a side elevational view of a rectal thermosensing unit according to a third alternate embodiment of the present invention with portions shown in section.

FIG. 10 is a cross-sectional view of the rectal thermosensing unit taken along lines 10—10 of FIG. 9.

DETAILED DESCRIPTION OF THE PREFERRED EMBODIMENTS

Figure 1:
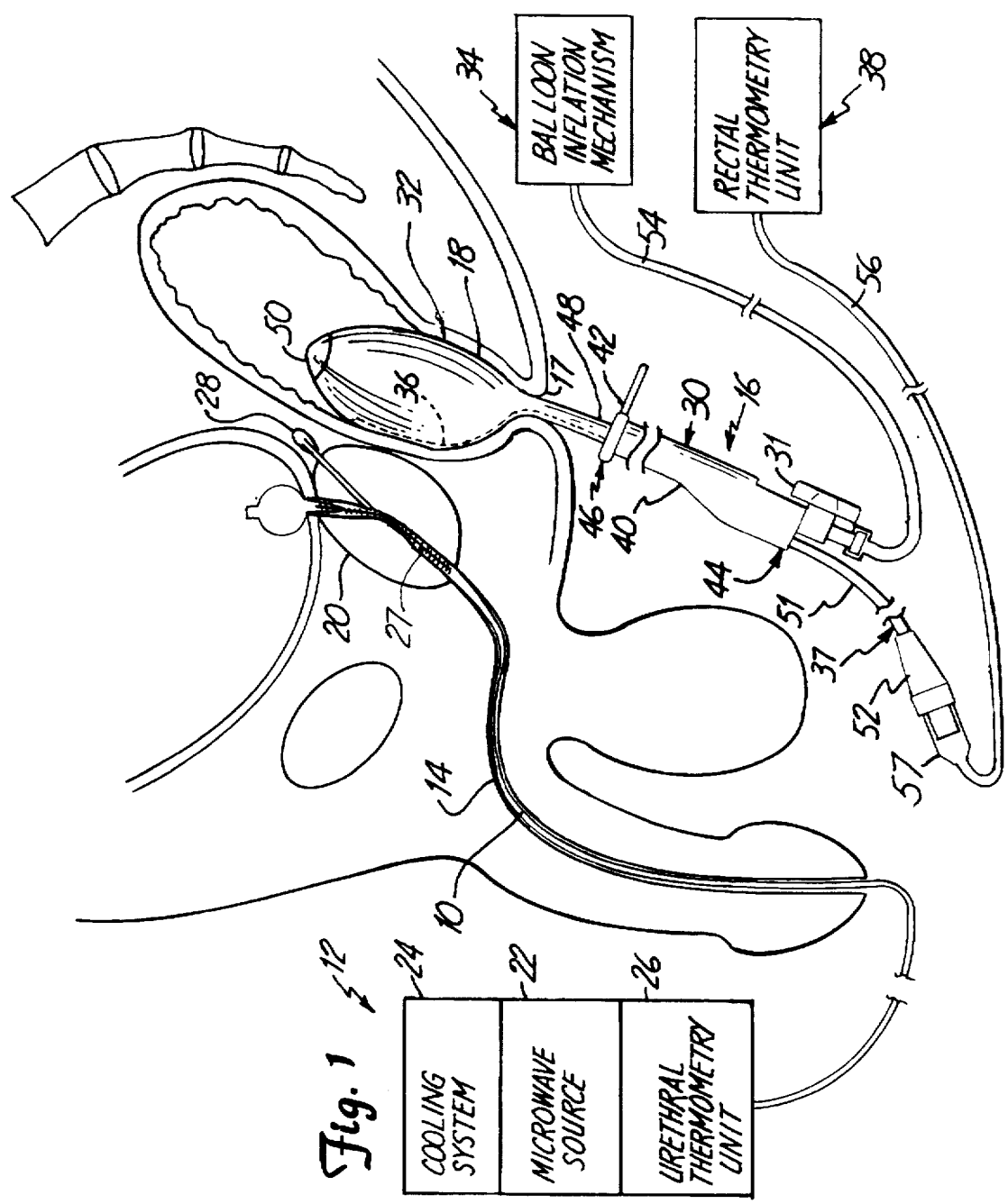
FIG. 1 is a vertical sectional view of a male pelvic region illustrating a transurethral thermal therapy device positioned in the urethra and a rectal thermosensing unit positioned within the rectum of the male pelvic region.

FIG. 1 is a vertical sectional view of a male pelvic region illustrating catheter 10 of transurethral thermal therapy system 12 properly positioned within urethra 14 and rectal thermosensing unit 16 properly positioned within rectum 18. Transurethral thermal therapy system 12 heats benign tumorous tissue growth within prostate 20 surrounding urethra 14 to necrose the tumorous tissue. Catheter 10 of transurethral thermal therapy system 12 preferably comprises a microwave antenna-containing catheter including a multilumen shaft. Transurethral thermal therapy system 12 further includes a microwave source 22, a cooling system 24 and a urethral thermometry unit 26. As described in further detail in U.S. Pat. No. 5,413,588 entitled DEVICE FOR ASYMMETRICAL THERMAL THERAPY WITH HELICAL DIPOLE MICROWAVE ANTENNA, assigned to Urologix, Inc. , which is incorporated by reference, transurethral thermal therapy system 12 treats benign tumorous tissue growth within prostate 20 with a microwave generating source 22, which energizes an antenna 27, located within catheter 10 and positioned within urethra 14 across prostate 20. Energization of antenna 27 causes antenna 27 to emit electromagnetic energy which heats tissue within prostate 20. To avoid unnecessary and undesireous damage to urethra 10 and adjacent healthy tissues, such as ejaculatory duct 28 and rectum 18, cooling system 24 supplies a cooling fluid through the multi-lumen shaft of catheter 10 to precisely control temperature distribution of tissue surrounding catheter 10 based upon temperatures of the tissues sensed by urethral thermometry unit 26.

To further measure and monitor the temperature of tissue adjacent prostate 20 so as to prevent unnecessary damage to otherwise healthy tissue surrounding prostate 20, rectal thermosensing unit 16 is positioned within rectum 18 adjacent prostate 20. Rectal thermosensing unit 16 generally includes handle 30, control valve 31, balloon 32, balloon inflation mechanism 34, temperature sensing device 36, sensing device connector assembly 37 and rectal thermometry unit 38. Handle 30 is a generally elongate member having a central body 40 and a flag 42. Central body 40 includes a first end 44 and a second end 46. First end 44 of central body 40 is positioned adjacent control valve 31 and connector assembly 37. Second end 46 of handle 30 is coupled to balloon 32 and temperature sensing device 36. Central body 40 preferably has a length extending between first end 44 and second end 46 sized for allowing a physician to easily grasp handle 30. Handle 30 preferably has a length of about 6.5 inches and a diameter of about 0.5 inches. Handle 30 enables a physician to easily manipulate balloon 32 and temperature sensing device 36 for properly positioning temperature sensing device 36 within rectum 18 adjacent prostate 20.

Flag 42 generally comprises an elongate protrusion radially extending outward from central body 40 at a selected angle or position relative to balloon 32 and temperature sensing device 36. Flag 42 is located at the second end 46 of handle 30 and indicates the orientation of balloon 32 and temperature sensing device 36 within rectum 18. Flag 42 further indicates when balloon 32 and temperature sensing device 36 have been fully inserted into rectum 18. As can be appreciated, a variety of indicating mechanisms such as indexing marks, grooves or alternative projections may be used in lieu of flag 42 for permitting a physician to visually determine the orientation and location of balloon 32 and temperature sensing device 36 within rectum 18.

Control valve 31 preferably comprises a standard stop cock for regulating inflation of balloon 32 by balloon inflation mechanism 34. Control valve 31 is attached to handle 30 and is fluidly coupled to an inflation lumen 60 (shown in FIGS. 2 and 3) extending through handle 30. Control valve 31 regulates the flow of inflation fluid from balloon inflation mechanism 34 through inflation lumen 60 into balloon 32. Because control valve 31 is positioned adjacent handle 30, a physician may easily manipulate balloon 32 while also adjusting the rate of inflation of balloon 32.

Balloon 32, upon inflation, is a generally oval-shaped balloon having a first end 48 and a second end 50. First end 48 of balloon 32 is coupled to second end 46 of handle 30. In the preferred embodiment, balloon 32 is manufactured from a flexible, elastic material such as 50 durometer silicone. Balloon 32 is coupled to and supports temperature sensing device 36 and independently functions as a rectal probe itself without requiring any further supporting structure within its interior. As a result, the rectal probe consisting of balloon 32 and its associated temperature sensing device 36 has a lower overall weight and better maintains its positioning within the rectum. Because balloon 32 is oval-shaped, balloon 32 has an extremely large surface area which may be positioned in contact with the rectal tissue upon inflation. Consequently, balloon 32, upon inflation, sufficiently engages the wall of the rectum to maintain balloon 32 and temperature sensing device 36 within the rectum during treatment without severely compressing rectal tissue to prevent damage to the rectal tissue during treatment.

Figure 8:
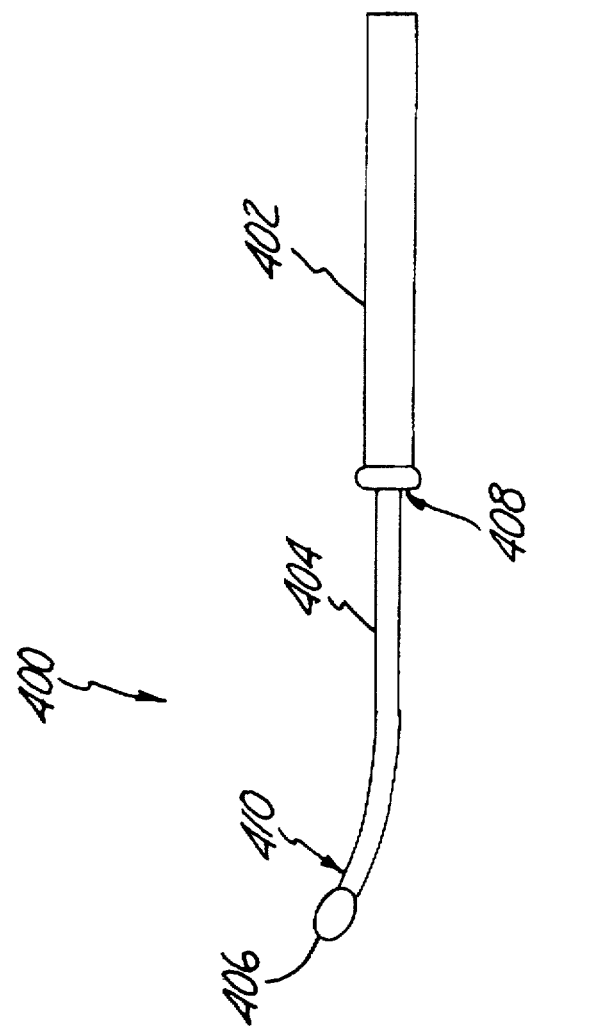
FIG. 8 is a side elevational view of an insertion device for introducing and inserting into the rectum the rectal thermosensing unit of the present invention.

Prior to treatment, balloon 32 is inserted into rectum 18 by an insertion device such as shown in FIGS. 8 and 9. Alternatively, balloon 32 may be digitally inserted into rectum 18 by a physician. Once inserted into rectum 18, balloon 32 is inflated by balloon inflation mechanism 34. Balloon inflation mechanism 34 preferably inflates balloon 32 with a gas such as air to a selected inflation volume and pressure so as to cause balloon 32 to assume its oval-shape as closely as possible and to engage the rectal wall without compressing adjacent tissue. Because balloon 32 is preferably inflated with a gas such as air, rather than an ionic solution, the temperature effects of the inflation medium upon the temperature sensing device 36 are minimized, resulting in more accurate temperature measurements. In addition, because balloon 32 is preferably inflated with a gas, rather than a liquid, balloon 32 is lighter in weight and better maintains its positioning within the rectum. Upon being inflated by balloon inflation mechanism 34, balloon 32 positions and maintains temperature sensing device 36 in contact with tissue of rectum 18 adjacent prostate 20.

Balloon inflation mechanism 34 is conventionally known and includes an inflation lumen 54 which is in fluid communication with an interior of balloon 32. Balloon inflation mechanism 34 supplies pressurized fluid, preferably a gas such as air, through inflation lumen 54 into the interior of balloon 32 to inflate balloon 32 to a desired size and pressure.

Temperature sensing device 36 preferably comprises an elongate strip of a plurality of temperature sensors which are supported along an exterior surface of balloon 32. Temperature sensing device 36 extends between first end 48 and second end 50 of balloon 32 and senses temperature of tissue of rectum 18 proximate prostate 20. Temperature sensing device 36 is electrically connected to rectal thermometry unit 38 by sensing device connector assembly 37 so as to transmit signals correlating to sensed temperatures to rectal thermometry unit 38.

Sensing device connector assembly 37 connects temperature sensing device 36 and rectal thermometry unit 38 and includes cable 51 and connector 52. Cable 51 preferably extends through central body 40 of handle 30 and has a first end connected to temperature sensing device 36 and a second end electrically connected to connector 52. Connector 52 preferably comprises a standard eight pin connector configured for mating with a corresponding connector of rectal thermometry unit 38.

Rectal thermometry unit 38 is conventionally known and includes cable 56 and connector 57. Connector 57 mates with connector 52 to electrically connect temperature sensing device 36 to rectal thermometry unit 38 for the transmission of electrical signals corresponding to sensed temperature values. Rectal thermometry unit 38 receives signals from temperature sensing device 36 and converts the signals into temperature values of the tissue of rectum 18. The temperature values may be displayed and/or transmitted to transurethral thermal therapy system 12 for closed loop temperature control of system 12.

Figure 3:
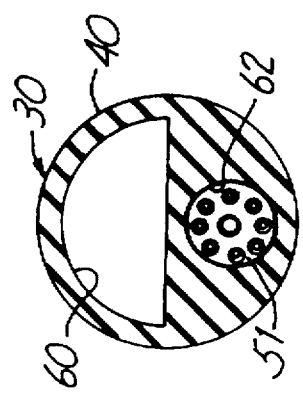
FIG. 3 is a cross-sectional view of the rectal thermosensing unit taken along lines 3—3 of FIG. 2.
Figure 2:
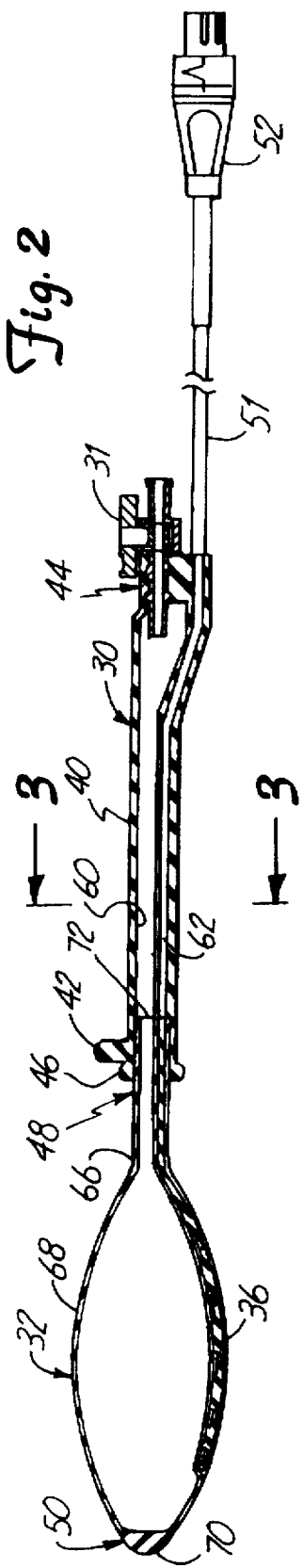
FIG. 2 is a side elevational view of the rectal thermosensing unit of FIG. 1 with portions shown in section.

FIGS. 2 and 3 illustrate handle 30, balloon 32 and temperature sensing device 36 in greater detail. FIG. 2 is a side elevational view of thermosensing unit 16 with handle 30 and balloon 32 shown in section to illustrate the relationship between handle 30 and balloon 32 in greater detail. FIG. 3 is a cross-sectional view taken along lines 3—3 of FIG. 2 illustrating handle 30 in greater detail. As best shown by FIGS. 2 and 3, central body 40 of handle 30 defines a pair of isolated lumens 60 and 62. Lumen 60 extends through body 40 of handle 30 from first end 44 to second end 46 of handle 30. Lumen 60 is in fluid communication with control valve 31 and the interior of balloon 32. Lumen 60 is preferably sized for transmitting a pressurized fluid from balloon inflation mechanism 34 (shown in FIG. 1) into the interior of balloon 32 to inflate balloon 32.

Lumen 62 extends substantially parallel to lumen 60 along the length of handle 30 from first end 44 to second end 46. Lumen 62 is sized for receiving sensor cable 51. As shown by FIG. 2, sensor cable 51 extends through lumen 62 from below control valve 31 to temperature sensing device 36 at second end 46 of handle 30.

As best shown by FIG. 2, balloon 32 includes neck 66, body or head 68 and nose 70. Neck 66, head 68 and nose 70 of balloon 32 are preferably integrally formed as part of a unitary structure of the same material. Neck 66 is coupled to head 68 so as to be substantially positioned inside the rectum when head 68 is positioned within the rectum. Neck 66 integrally extends from head 68 towards first end 48. Neck 66 has a narrower diameter than head 68. As a result, balloon 32 better maintains its position within the rectum upon inflation. Neck 66 has a diameter sized only for accommodating sensor assembly 36 and inflation lumen 60 to sufficiently transfer an inflation medium into balloon 32. Consequently, neck 66 has a small diameter enabling easier and less traumatic insertion of balloon 32 and providing greater comfort to the patient. Neck 66 includes a port 72 which is located within end 46 of handle 30. Portions of neck 66 that are located within handle 30 are preferably sealed to handle 30 to prevent escape of inflation medium between neck 66 and handle 30. Port 72 is in fluid communication with lumen 60 of handle 30.

Head 68 of balloon 32 has a narrower diameter at both neck 66 and nose 70. Head 68 defines a void interior for the reception of an inflation medium. Because the interior is void of any additional supporting structures, balloon 32 is lightweight, enabling balloon 32 to better maintain its positioning within the rectum. Head 68 of balloon 32 preferably has a nominal inflation volume of about 120 cc and a nominal diameter of about 1.9 inches. Head 68 supports temperature sensing device 36 against the tissue of rectum 18 as shown in FIG. 1. Nose 70 is located at a second end 50 of balloon 32 and preferably has an increased thickness relative to head 68 so as to also have an increased stiffness and rigidity for providing easier insertion of balloon 32 through anus 17 (shown in FIG. 1) into rectum 18.

FIGS. 4 and 5 illustrate balloon 32 and temperature sensing device 36 in greater detail. FIG. 4 is a perspective view of second end 46 of handle 30, balloon 32 and temperature sensing device 36. For purposes of illustration, temperature sensing devices are shown as being partially separated from balloon 32. FIG. 5 is a cross-sectional view taken along lines 5—5 of FIG. 4. As best shown by FIG. 4, neck 66 and head 68 of balloon 32 define an elongate channel or groove 76 which extends from first end 48 of balloon 32 towards second end 50. Groove 76 extends along an outer surface of balloon 32 and has a depth approximately equal to a height of temperature sensing device 36. The recess formed by groove 76 substantially receives temperature sensing device 36 so that temperature sensing device 36 does not project out of groove 76. As a result, groove 76 maintains temperature sensing device 36 in place. In addition, groove 76 enables balloon 32 to support temperature sensing device 36 along an outer surface of balloon 32 while maintaining a substantially smooth exterior surface contour. The substantially smooth exterior surface contour of balloon 32 provides for easier insertion of balloon 32 and temperature sensing device 36 into rectum 18 and prevents possible trauma or damage to rectum tissue otherwise brought about by sharp projecting edges.

As further shown by FIG. 4, temperature sensing device 36 includes a plurality of temperature sensors 78, flexible circuit 79 and sensor protective strip 80. Temperature sensors 78 preferably comprise resistance temperature device (RTD) type sensors. Alternatively, sensors 78 may comprise any of a variety of conventional temperature sensing devices such as thermocouples and thermistors. Sensors 78 are preferably bonded to flexible circuit 79 and are spaced apart from one another along flexible circuit 79 and along sensor protective strip 80 by about 0.6 inches. Sensors 78 individually sense the temperature of tissue adjacent to and along balloon 32.

Flexible circuit 79 electrically connects temperature sensors 78 and cable 51. Flexible circuit 79 generally comprises an elongate strip of a dielectric material such as a polyimide or polyester. Flexible circuit 79 preferably is made of KAPTON by Dupont. Flexible circuit 79 includes conductive traces 81. Conductive traces 81 generally consist of lines or traces of conductive material such as copper or silver which are deposited or fabricated upon or within the dielectric material of flexible circuit 79. Conductive traces 81 are electrically connected, preferably by soldering, to electrical leads of temperature sensor 78 and cable 51. Conductive traces 81 electrically connect temperature sensor 78 to cable 51 so that signals corresponding to sensed temperature values may be transmitted from temperature sensors 78 through cable 51 to rectal thermometry unit 38 (shown in FIG. 1).

Sensor protective strip 80 is an elongate strip extending from second end 46 of handle 30. Sensor protective strip 80 is preferably made from a flexible material, such as a silicone material. As best shown by FIG. 5, sensor protective strip 80 encapsulates and encloses sensors 78 and flexible circuit 79 to protect sensors 78 and flexible circuit 79 from damage. Sensor protective strip 80 also covers sensors 78 and flexible circuit 79 to provide a relatively smooth, flat surface over sensors 78 and flexible circuit 79 along an exterior of balloon 32 to prevent damage to rectum tissue during insertion and use of rectal thermosensing unit 16. Because sensor protective strip 80 permits sensor 78 to be supported by balloon 32 along an exterior surface of balloon 32, rectal thermosensing unit 16 is less complex and easier to manufacture.

Sensor protective strip 80 is preferably formed from the same or similar material forming handle 30 and is preferably encapsulated within handle 30 as part of a unitary structure. Because sensor protective strip 80 is preferably encapsulated within handle 30, sensor protective strip 80 more reliably maintains the position of sensor 78 along the outer surface of balloon 32 without the risk of sensors 78, flexible circuit 79 or sensor protective strip 80 becoming severed or torn away from handle 30 while within rectum 18.

As best shown by FIG. 4, sensor protective strip 80 includes a plurality of notches or perforations 82 positioned at spaced apart intervals between a first end 84 and a second end 86 of sensor protective strip 80. Perforations 82 extend into the flexible material of sensor protective strip 80 and provide increased flexibility to sensor protective strip 80 to facilitate positioning of sensor 78 adjacent rectal tissue. As further shown by FIG. 4, first end 84 of sensor protective strip 80 is coupled to handle 30. Adhesive 88 is preferably applied along the entire length of strip 80 between strip 80 and groove 76 to bond strip 80 within groove 76. As can be appreciated, sensor protective strip 80 may be secured or bonded within groove 76 of balloon 32 by any one of a variety of adhesives or other well-known attachment methods.

Figure 7:
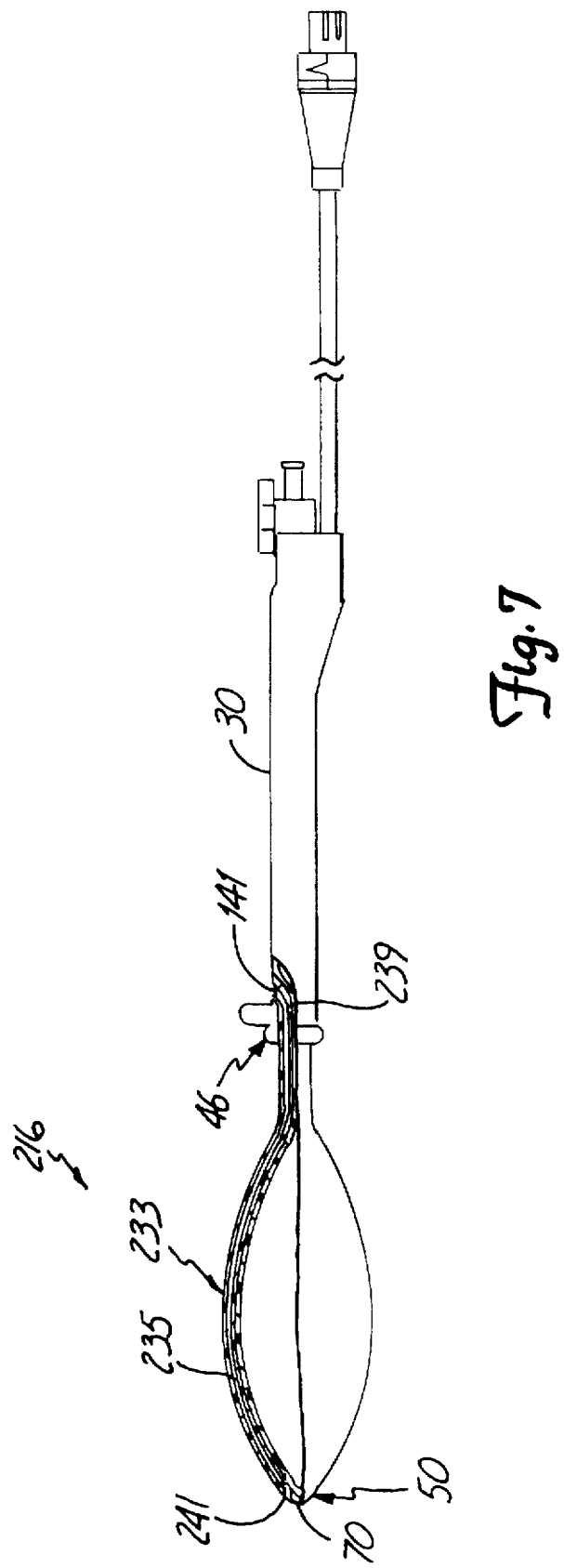
FIG. 7 is a side elevational view of a rectal thermosensing unit according to a second alternate embodiment of the present invention with portions shown in section.

FIGS. 6 and 7 illustrate thermosensing units 116 and 216, alternate embodiments of thermosensing unit 16. FIG. 6 is a side elevational view of thermosensing unit 116 with portions shown in section. For ease of illustration, those elements of thermosensing unit 116 which are the same as elements of thermosensing unit 16 are numbered similarly. As shown by FIG. 6, thermosensing unit 116 is similar to thermosensing unit 16 except that thermosensing unit 116 additionally includes a ventilation passageway 133 for a passage of air or gas around and through balloon 32 to relieve pressure in the rectum during treatment. Ventilation passageway 133 preferably includes ventilation channel 135 and ventilation conduit 139 which are in communication with one another to form ventilation passageway 133. Ventilation channel 135 is a generally U or C-shaped panel, slot or groove formed along an exterior surface of balloon 32. Ventilation channel 135 preferably extends from nose 70 located at second end 50 of balloon 32 to second end 46 of handle 30. Ventilation channel 135 preferably is located opposite or approximately 180 degrees from groove 76 (shown in FIG. 4) of balloon 32. Ventilation channel 135 preferably extends sufficiently into handle 30 so as to communicate with ventilation conduit 139. Ventilation channel 135 preferably has sidewalls of sufficient stiffness to prevent the total collapse of channel 135 when pressed against walls of the rectum of the patient. Ventilation channel 135 is preferably sized so as to have a sufficient depth and width for providing adequate passage of gas or air to relieve pressure within the rectum.

Ventilation conduit 139 extends from proximate second end 46 of handle 30 towards first end 44 of handle 30 past flag 42 and terminates at vent hole 141. Ventilation conduit 141 preferably has a diameter sufficient for permitting adequate passage of gas to relieve pressure within the rectum of the patient. As can be appreciated, although illustrated as constituting a bore extending through handle 30, ventilation conduit 141 may also be formed as a channel or groove in the exterior surface of handle 30.

Ventilation channel 135 and ventilation conduit 139 communicate with one another to form ventilation passageway 133. Because ventilation channel 135 extends along an exterior of balloon 32 substantially from second end 50 to first end 48, ventilation channel 135 permits gas built-up within the rectum of the patient to easily escape through channel 135 and through ventilation conduit 139. As a result, gas passage 133 provides for unobstructed escape of gas for greater patient comfort during treatment.

FIG. 7 illustrates rectal thermosensing unit 216. Rectal thermosensing unit 216 is similar to rectal thermosensing unit 116 except that rectal thermosensing unit 216 includes ventilation passageway 233 in lieu of ventilation passageway 133. Ventilation passageway 233 is similar to ventilation passageway 133 except that ventilation passageway 233 includes ventilation tube 235 in lieu of ventilation channel 135. Ventilation tube 235 is an elongate tubular member formed from a soft, flexible material such as silicone and having a diameter sized for permitting sufficient passage of gas to relieve pressure within the rectum of the patient. Ventilation tube 235 preferably extends from nose 70 on second end 50 of balloon 32 to second end 46 of handle 30 so as to communicate with ventilation conduit 239. Ventilation tube 235 preferably is located opposite or approximately 180 degrees with respect to groove 76 (shown in FIG. 4) formed in balloon 32. Because ventilation tube 235 extends from second end 50 of balloon 32, which is preferably tapered towards nose 70, opening 241 of tube 235 is less likely to contact and become obstructed by walls of the rectum of the patient. Thus, gas otherwise trapped within the rectum of the patient is permitted to escape through opening 241 and through ventilation tube 235 and ventilation conduit 239 of ventilation passageway 233 to relieve pressure within the rectum. Thus, rectal thermosensing unit 216 provides for greater patient comfort during treatment. As can be appreciated, ventilation tube 235 may alternatively extend through an interior of balloon 32.

FIG. 8 is a side elevational view illustrating insertion device 400 that may used to introduce and insert balloon 32 into rectum 18 (shown in FIG. 1). Insertion device 400 generally includes handle 402, shaft 404 and tip 406. Handle 402 is an elongate cylindrical member sized for being easily grasped by a physician. Preferably, handle 402 has a diameter of 0.5 to 1.5 inches and a length of 5.0 to 10.0 inches.

Shaft 404 is a generally elongate cylindrical or tubular member having a stiffness sufficient to enable balloon 32 to be adequately inserted and positioned within the rectum of the patient. At the same time, shaft 404 preferably has adequate flexibility to insure patient comfort. Shaft 404 extends from handle 402 and includes a first end 408 fixedly coupled to handle 402 and a second end 410 fixedly coupled to tip 406. End 408 preferably extends axially from handle 402. End 410 preferably diverges away from the axial center line of end 408 and handle 402 at an angle of between about 0 degrees to 50 degrees. In the most preferred embodiment, end 410 diverges from the axial center line of handle 402 at an angle of 25 degrees. Shaft 404 preferably has a length sufficient for adequately positioning balloon 32 within the rectum of the patient without the balloon inverting and a diameter adequate to provide sufficient stiffness yet small enough for patient comfort. Shaft 404 preferably has a length of between about 3.0 to 7.0 inches (a length greater than the length a physician's finger otherwise used for digital insertion) and a diameter of about 0.1 to 0.5 inches.

Tip 406 is a generally oval-shaped, round and smooth bulbous member fixedly coupled to end 410 of shaft 404. Tip 406 preferably has a diameter of between about 0.2 to about 1.0 inches. Tip 406 supports balloon 32 (shown in FIG. 1) and initially penetrates the opening of the rectum for insertion of the balloon into the rectum. In particular, tip 406 is positioned adjacent balloon 32 (shown in FIG. 1) while force is applied to handle 402 so that tip 406 forces balloon 32 into the rectum. Once balloon 32 is properly positioned within the rectum, tip 406 and shaft 404 are removed from the rectum by manipulation of handle 402. Overall, insertion device 400 enables rectal thermosensing units 16, 116 and 216 to be more easily introduced within the rectum. Because rectal thermosensing units 16, 116 and 216 each include supple, rectal conforming balloons that support temperature sensors and have void interiors, the balloons of rectal thermosensing units 16, 116 and 216 measure rectal wall temperature without displacing the rectal wall, thus ensuring adequate blood circulation within the tissue of the rectal wall and minimum deformation of the rectal wall and prostate region. Although the suppleness of the balloon and the void interior of the balloon enable accurate temperature measurements of the rectal wall to be taken without reducing blood circulation in the rectal wall and without affecting the area of the prostate region being heated, the balloons of rectal thermosensing units 16, 116 and 216 may be difficult to introduce within the rectum. Digital is often inadequate and causes the balloon to invert. Insertion device 400 solves the associated problems with digital insertion while constituting a removable, separate element from the balloon so that the balloon of rectal thermosensing units 16, 116 and 216 better maintains its original position and more accurately measures rectal wall temperature without displacing the rectal wall. As can be appreciated, shaft 404 and tip 406 of insertion device 400 may have various lengths, diameters and shapes as desired depending upon the size and configuration of the balloon, such as balloon 32, being inserted into the rectum.

Rectal thermosensing units 16, 116 and 216 provide several desirable advantages. Because balloon 32 is oval-shaped, balloon 32, upon inflation, has a large surface area for sufficiently engaging the rectum wall to maintain balloon 32 and temperature sensing device 36 within the rectum during treatment without severely compressing the rectal tissue. As a result, the rectal tissue is less susceptible to thermal damage during treatment. Because first end 48 of balloon 32 extends from the end 46 of handle 30, rectal thermosensing unit 16 does not include a probe extending through balloon 32 which may traumatize and damage rectal tissue within the rectum during insertion of the balloon. In addition, because balloon 32 defines an interior void of any supporting structures, balloon 32 is lightweight, enabling balloon 32 and temperature sensing device 36 to better maintain their positioning within the rectum. Furthermore, because head 68 of balloon 32 is wider than neck 36, balloon 32 maintains its position within rectum 18 and is less susceptible to becoming dislodged or repositioned within the rectum.

In addition, the configuration of handle 30 and fluid control valve 31 enables the physician to more easily and accurately position balloon 32 within rectum 18 and to inflate balloon 32 to a proper size and pressure. Flag 42 of handle 30 allows the physician to easily determine the orientation and location of balloon 32 within rectum 18. Because fluid control valve 31 is located adjacent handle 30, the physician may easily adjust the inflation pressure and size of balloon 32.

Lastly, balloon 32 and temperature sensing device 36 cause less discomfort to the patient upon insertion and are easily manufactured and assembled. Because temperature sensing device 36 is mounted or secured along an exterior surface of balloon 32, rectal thermosensing unit 16 is more easily and less expensively manufactured. In addition, groove 76 receives temperature sensing device 36 to maintain the position of temperature sensing device 36 along balloon 32 and to give balloon 32 a generally smooth outer contour despite the presence of temperature sensing device 36. As a result, groove 76 prevents temperature sensing device 36 from causing damage to rectum tissue upon insertion. Because sensor protective strip 80 encloses and covers sensor 78 and flexible circuit 79, sensor protective strip 80 provides a smooth, preferably soft, outer surface which is less likely to damage rectum tissue. Rectal thermosensing units 116 and 216 additionally provide ventilation passageways for permitting the escape of air or gas within the rectum of the patient to relieve pressure build-up. Because sensor protective strip 80 is preferably integrally formed with handle 30 as part of a unitary structure, sensor protective strip 80 more reliably maintains the positions of sensors 78 along the outer surface of balloon 32 without the risk of sensor protective strip 80 becoming severed or torn away from handle 30 while within rectum 18.

FIGS. 9 and 10 illustrate rectal thermosensing unit 516, an alternate embodiment of rectal thermosensing unit 116. FIG. 9 is a side elevational view of rectal thermosensing unit 516 with portions shown in section for illustration purposes. FIG. 10 is a cross-sectional view of rectal thermosensing unit 516 taken along lines 10—10 of FIG. 9. Those elements of rectal thermosensing unit 516 which are the same as corresponding elements of rectal thermosensing unit 116 are numbered similarly. Rectal thermosensing unit 516 is similar to rectal thermosensing unit 116 except that rectal thermosensing unit 516 includes balloon 532 in lieu of balloon 32. Balloon 532 includes neck 566, head 568 and nose 570 which are preferably integrally formed as part of a unitary structure of the same material. Neck 566 is coupled to head 568 so as to be substantially positioned inside the rectum when head 568 is positioned within the rectum. Neck 566 integrally extends from head 568 towards first end 48. Neck 566 has a narrower diameter than head 568. As a result, balloon 532 better maintains its position within the rectum upon inflation. Neck 566 has a diameter sized for accommodating ventilation channel 535, lumen 560 and sensor cable 51. Neck 566 includes a port 72 which is located within end 46 of handle 30. Portions of neck 566 located within handle 30 are preferably sealed to handle 30 to prevent escape of inflation fluid between neck 566 and handle 30. Port 72 is in fluid communication with lumen 60 of handle 30.

Head 568 of balloon 32 has a narrower diameter at both neck 566 and nose 570. Head 568 preferably has a nominal inflation volume of about 120 cc and a nominal diameter of about 1.9 inches. Head 568 supports temperature sensing device 36 (shown in FIGS. 4 and 5) against the tissue of rectum 18 as shown in FIG. 1. Nose 570 is located at a second end 50 of balloon 532 and preferably has an increased thickness relative to head 568 so as also have an increased stiffness and rigidity for providing easier insertion of balloon 532 through anus 17 (shown in FIG. 1) into rectum 18.

Ventilation shaft 572 extends through balloon 532 from nose 570 through head 568 and neck 566 into end 46 of handle 30. Ventilation shaft 572 defines ventilation channel 535 which extends from opening 541 located at nose 570 to ventilation conduit 539 which extends through handle 30 past end 46. Ventilation passageway 533 including channel 535 of ventilation shaft 572 and conduit 539 permits gas trapped within the rectum to escape through opening 541 and through ventilation passageway 535 out ventilation conduit 539 to relieve pressure within the rectum. Because ventilation passageway 533 is defined by ventilation shaft 572 which extends through balloon 532, ventilation passageway 533 is less likely to contact and become obstructed by walls of the rectum of the patient.

In addition to defining ventilation passageway 533, ventilation shaft 572 also supports balloon 532, in an uninflated state, while balloon 532 is inserted into rectum 18. Ventilation shaft 572 preferably is designed to exhibit high column strength for insertion of balloon 532 into rectum 18. At the same time, the ventilation shaft 572 is preferably flexible to reduce trauma during insertion. Ventilation shaft 572 is preferably formed from a sixty to an eighty durometer silicone. The silicone material forming ventilation shaft 572 is preferably reinforced with a braid of material having a higher degree of stiffness.

As best shown by FIG. 10, neck 566 of balloon 532 defines ventilation passageway 533, including ventilation channel 535, lumen 560 and sensor 36. Ventilation channel 535 of ventilation passageway 533 extends through neck 566 and communicates with ventilation conduit 539 for releasing trapped gases. Lumen 560 communicates between lumen 60 within handle 30 and the interior of balloon 532 for inflation of balloon 532. As shown by FIG. 4, sensor 36 continues through neck 566 until sensor 36 connects with sensor cable 62. Due to its configuration, neck 566 has a minimal diameter for enabling easier and less traumatic insertion of balloon 532 and providing greater comfort to the patient.

Although the present invention has been described with reference to preferred embodiments, workers skilled in the art will recognize that changes may be made in form and detail without departing from the spirit and scope of the invention.

What is claimed is:

1. A rectal thermosensing unit for sensing temperature of rectal tissue, the unit comprising:

an inflatable balloon having a first end, a second end and a wall defining an interior surface and an exterior surface of the balloon, a portion of the wall defining a groove in the exterior surface;

a handle coupled to the inflatable balloon; and a temperature sensing device connected to the balloon within the groove.

2. The rectal thermosensing unit of claim 1, wherein the temperature sensing device comprises:

a flexible circuit member;

a temperature sensor supported on the flexible circuit member; and a protective strip encapsulating the flexible circuit member and the temperature sensor, the protective strip cooperating with the exterior surface of the balloon to provide a substantially smooth outer contour of the balloon.

3. The rectal thermosensing unit of claim 2, wherein the protective strip is fixedly adhesively bonded to the groove in the exterior surface of the balloon.

4. The rectal thermosensing unit of claim 2, wherein the temperature sensing device further comprises a plurality of temperature sensors supported on the flexible circuit member and spaced from each other along a length of the flexible circuit member.

5. The rectal thermosensing unit of claim 4, further comprising conductive traces on the flexible circuit member for electrically connecting to the plurality of temperature sensors and to thermometry circuitry external to the balloon and the temperature sensing device.

6. The rectal thermosensing unit of claim 2, wherein the protective strip includes a plurality of notches positioned at spaced intervals along a length of the protective strip.

7. A rectal thermosensing unit for sensing temperature of rectal tissue, the unit comprising:

an inflatable balloon having a first end, a second end and a wall defining an interior of the balloon, the balloon having an exterior surface extending between the first end and the second end of the balloon;

a handle coupled to the inflatable balloon;

a temperature sensing device having a height; and a groove in the exterior surface of the inflatable balloon having a depth no less than the height of the temperature sensing device, the groove receiving the temperature sensing device so that inflation of the balloon positions and maintains the temperature sensing device in proximal contact with a rectal wall while preventing the temperature sensing device from projecting beyond the exterior surface of the balloon.

8. The rectal thermosensing unit of claim 7, wherein the temperature sensing device comprises:

a flexible circuit member;

a temperature sensor supported on the flexible circuit member; and a protective strip encapsulating the flexible circuit member and the temperature sensor, the protective strip cooperating with the exterior surface of the balloon to provide a substantially smooth outer contour of the balloon.

9. The rectal thermosensing unit of claim 8, wherein the protective strip is fixedly adhesively bonded to the groove in the exterior surface of the balloon.

10. The rectal thermosensing unit of claim 8, wherein the temperature sensing device further comprises a plurality of temperature sensors supported on the flexible circuit member and spaced from each other along a length of the flexible circuit member.

11. The rectal thermosensing unit of claim 10, further comprising conductive traces on the flexible circuit member for electrically connecting to the plurality of temperature sensors and to thermometry circuitry external to the balloon and the temperature sensing device.

12. The rectal thermosensing unit of claim 8, wherein the protective strip includes a plurality of notches positioned at spaced intervals along a length of the protective strip.

* * * * *